United States Patent
Tsuji et al.

(10) Patent No.: US 7,153,988 B2
(45) Date of Patent: Dec. 26, 2006

(54) 7α-HYDROXY-PREGN-4-EN-3-ONE-20-CARBALDEHYDE, PROCESS FOR PRODUCING THE SAME, AND PROCESS FOR PRODUCING 7α, 21-DIHYDROXY-20-METHYL-PREGN-4-EN-3-ONE FROM THE SAME

(75) Inventors: Masao Tsuji, Kurashiki (JP); Yoko Nakano, Kurashiki (JP); Shigeo Ohzono, Kurashiki (JP); Makoto Nakazawa, Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 477 days.

(21) Appl. No.: 10/488,808

(22) PCT Filed: Jul. 30, 2002

(86) PCT No.: PCT/JP02/07737

§ 371 (c)(1),
(2), (4) Date: Mar. 4, 2004

(87) PCT Pub. No.: WO03/023047

PCT Pub. Date: Mar. 20, 2003

(65) Prior Publication Data

US 2004/0236126 A1    Nov. 25, 2004

(30) Foreign Application Priority Data

Sep. 4, 2001   (JP) .............................. 2001-267025
Sep. 14, 2001  (JP) .............................. 2001-279249

(51) Int. Cl.
  *C07J 9/00*  (2006.01)

(52) U.S. Cl. ..................................... 552/553

(58) Field of Classification Search ................. 552/553
  See application file for complete search history.

(56) References Cited

U.S. PATENT DOCUMENTS 4,867,914 A * 9/1989 Bunno et al. ............... 552/553
5,112,998 A   5/1992 Tsuji et al.
2003/0181742 A1 9/2003 Nakazawa et al.

FOREIGN PATENT DOCUMENTS

| JP | 58-224691 A | 12/1983 |
|----|-------------|---------|
| JP | 2525049 B2  | 5/1996  |
| WO | WO 94/19366 A1 | 9/1994 |
| WO | WO 98/24800 * | 6/1998 |
| WO | WO 98/24800 A2 | 6/1998 |
| WO | WO 02/20552 A1 | 3/2002 |

OTHER PUBLICATIONS

Dutta et al., *Applied and Environmental Microbiology*, 64 (5), 1884-1889 (May 1998).
Jones et al., *J. Org. Chem.*, 63, 3786-3789 (1998).
Kinney et al., *Organic Letters*, 2 (19), 2921-2922 (2000).
Moriarty et al., *Tetrahedron Letters*, 35 (44), 8103-8106 (1994).
Pechulis et al., *J. Org. Chem.*, 60, 5121-5126 (1995).
Zhang et al., *J. Org. Chem.*, 63, 8599-8603 (1998).

* cited by examiner

*Primary Examiner*—Barbara P. Badio
(74) *Attorney, Agent, or Firm*—Leydig, Voit & Mayer, Ltd.

(57) ABSTRACT

7α-Hydroxy-pregn-4-en-3-one-20-carbaldehyde, a production method thereof and a method for producing 7α,21-dihydroxy-20-methyl-pregn-4-en-3-one, which is useful as a synthetic intermediate for pharmaceuticals such as squalamine and the like, efficiently at high purity from the carbaldehyde.

7 Claims, No Drawings

7α-HYDROXY-PREGN-4-EN-3-ONE-20-CARBALDEHYDE, PROCESS FOR PRODUCING THE SAME, AND PROCESS FOR PRODUCING 7α, 21-DIHYDROXY-20-METHYL-PREGN-4-EN-3-ONE FROM THE SAME

TECHNICAL FIELD

The present invention relates to 7α-hydroxy-pregn-4-en-3-one-20-carbaldehyde represented by the formula (I)

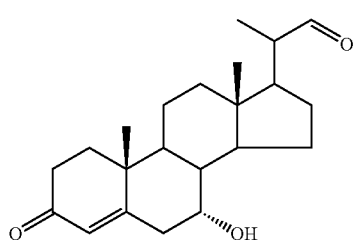

(I)

a production method thereof and a production method of 7α,21-dihydroxy-20-methyl-pregn-4-en-3-one represented by the formula (II)

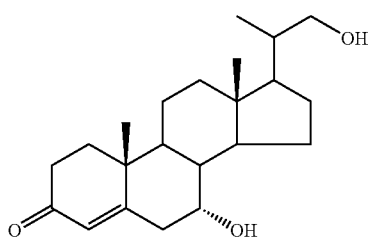

(II)

using said 7α-hydroxy-pregn-4-en-3-one-20-carbaldehyde.

7α-Hydroxy-pregn-4-en-3-one-20-carbaldehyde and 7α,21-dihydroxy-20-methyl-pregn-4-en-3-one provided by the present invention are useful as, for example, synthetic intermediates for pharmaceuticals, such as squalamine represented by the following formula Squalamine has been reported to have a potent antibacterial activity against Gram-positive bacteria, Gram-negative bacteria, fungi and the like, as well as an anticancer activity, and is a compound drawing attention as a new antibiotic [see J. Org. Chem., Vol. 63, p. 3786 (1998); J. Org. Chem., Vol. 63, p. 8599 (1998); WO98/24800 and the like].

BACKGROUND ART

Conventionally, squalamine has been extracted from the livers of dogfish sharks. Due to the extremely low extraction efficiency of 0.001–0.002 wt %, chemical synthesis methods thereof have been investigated. As chemical synthesis methods of squalamine, (1) a method using 3β-acetoxy-5-cholanic acid as a starting material [see Tetrahedron Lett., Vol. 35, p. 8103 (1994)], (2) a method using 3β-hydroxy-5-cholanic acid as a starting material [see J. Org. Chem., Vol. 60, p. 5121 (1995); WO 94/19366], (3) a method using 21-hydroxy-20-methyl-pregn-4-en-3-one as a starting material [see WO98/24800; Org. Lett., Vol. 2, p. 2921 (2000)] and (4) a method using stigmasterol as a starting material [see J. Org. Chem., Vol. 63, p. 3786 (1998); J. Org. Chem., Vol. 63, p. 8599 (1998); WO 98/24800] are known.

The 3β-acetoxy-5-cholanic acid, 3β-hydroxy-5-cholanic acid and 21-hydroxy-20-methyl-pregn-4-en-3-one used as starting materials in the above-mentioned method (1), method (2) and method (3), respectively, are all expensive. Moreover, reaction operations are complicated in that 17 steps are required in the above-mentioned method (1) and 19 steps are required in method (2) to obtain squalamine and the like. Therefore, these methods can be hardly said to be industrially advantageous production methods of squalamine.

On the other hand, in the above-mentioned method (4), stigmasterol used as a starting material can be obtained at a low price, but 20 steps are required to synthesize squalamine. Moreover, method (4) is associated with problems in that silver carbonate used in the step to selectively oxidize hydroxyl group at the 3-position is expensive, a special reaction equipment is necessary because an ozone oxidation step at a low temperature is included and the like, and cannot necessarily be said to be an industrially advantageous method, either.

It is therefore an object of the present invention to provide a compound useful as a synthetic intermediate for a pharmaceuticals such as squalamine and the like.

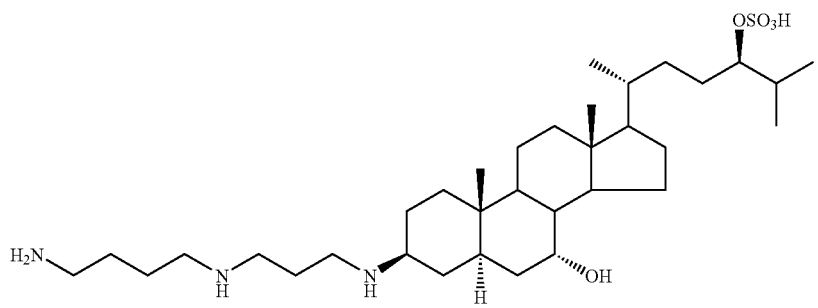

and the like.

Another object of the present invention is to provide a method capable of efficient production of the above-mentioned compound at high purity from an easily available starting material.

DISCLOSURE OF THE INVENTION

The present inventors have conducted intensive studies in an attempt to achieve the aforementioned objects and found that 7α-hydroxy-pregn-4-en-3-one-20-carbaldehyde, which is a novel compound, can be obtained efficiently at high purity by selecting 3α,7α-dihydroxy-5β-cholanic acid and/or a salt thereof as a starting material and subjecting the 3α,7α-dihydroxy-5β-cholanic acid and/or a salt thereof to a conversion reaction using a microorganism, and that 7α,21-dihydroxy-20-methyl-pregn-4-en-3-one can be produced efficiently at high purity by having a reducing agent act on said 7α-hydroxy-pregn-4-en-3-one-20-carbaldehyde, which resulted in the completion of the present invention.

The present invention provides 7α-hydroxy-pregn-4-en-3-one-20-carbaldehyde.

In addition, the present invention provides a production method of 7α-hydroxy-pregn-4-en-3-one-20-carbaldehyde, which comprises culturing a bacterium belonging to the genus *Pseudomonas*, which produces 7α-hydroxy-pregn-4-en-3-one-20-carbaldehyde from 3α, 7α-dihydroxy-5β-cholanic acid and/or a salt thereof as a substrate in a medium containing 3α,7α-dihydroxy-5β-cholanic acid and/or a salt thereof.

Moreover, the present invention provides a production method of 7α,21-dihydroxy-20-methyl-pregn-4-en-3-one, which comprises having a reducing agent act on 7α-hydroxy-pregn-4-en-3-one-20-carbaldehyde.

EMBODIMENT FOR CARRYING OUT THE INVENTION

The production method of 7α-hydroxy-pregn-4-en-3-one-20-carbaldehyde is explained first.

As the bacterium belonging to the genus *Pseudomonas*, for example, *Pseudomonas putida* D4014-A357-3A strain (FERM BP-8070) obtained by transmutation of *Pseudomonas putida* D4014 strain (FERM BP-205) can be mentioned.

The methological properties of *Pseudomonas putida* D4014 strain and *Pseudomdnas putida* D4014-A357-3A strain are shown in the following Table 1 and Table 2.

TABLE 1

| Mycological properties | *Pseudomonas putida* D4014 | *Pseudomonas putida* D4014-A357-3A |
|---|---|---|
| Microscopic observation | | |
| Form | Rods | Rods |
| Size | 0.5–0.6 × 1.5–2.9 μm | 0.5–0.6 × 1.5–2.9 μm |
| Flagella | Polar flagella | Polar flagella |
| Spore | None | None |
| Gram staining | Negative | Negative |
| Acid resistance | None | None |
| Observation of cultivation in medium | | |
| Bouillon agar plate culture | Round shape, prominent, convex circular, smooth, entire | Round shape, prominent, convex circular, smooth, entire |

TABLE 1-continued

| Mycological properties | *Pseudomonas putida* D4014 | *Pseudomonas putida* D4014-A357-3A |
|---|---|---|
| Bouillon agar slant medium | Moderate growth, filamentous, translucent, fluorescent | Moderate growth, translucent |
| Bouillon liquid culture | Turbid, thick film | Turbid, thick film |
| Growth temperature | Grown at 37° C. | Grown at 37° C. |
| Gelatin stab culture | No liquefaction | No liquefaction |
| Litmus milk | Alkaline, milk unchanged | Alkaline, milk unchanged |
| BCP milk | Alkaline, milk unchanged | Alkaline, milk unchanged |

TABLE 2

| Mycological properties | *Pseudomonas putida* D4014 | | *Pseudomonas putida* D4014-A357-3A | |
|---|---|---|---|---|
| Physiological properties (Note 1) | | | | |
| Reduction of nitrate | – | | – | |
| Denitrification | – | | – | |
| MR test | + | | + | |
| VP test | – | | – | |
| Generation of indole | – | | – | |
| Generation of hydrogen sulfide | – | | – | |
| Hydrolysis of starch | – | | – | |
| Utilization of citric acid | + | | + | |
| Utilization of inorganic nitrogen source | + | | + | |
| Urease | ± | | ± | |
| Oxydase | + | | + | |
| Catalase | + | | + | |
| Arginine dihydrolase | + | | + | |
| Behavior towards oxygen | Aerobic | | Aerobic | |
| O-F test | Oxidative | | Oxidative | |
| Behavior towards saccharides (Notes 2) | Generation of acid | Evolution of gas | Generation of acid | Evolution of gas |
| L-Arabinose | + | – | + | – |
| D-Xylose | + | – | + | – |
| D-Glucose | + | – | + | – |
| D-Mannose | + | – | + | – |
| D-Fructose | – | – | – | – |
| D-Galactose | + | – | + | – |
| Maltose | – | – | – | – |
| Sucrose | – | – | – | – |
| Lactose | – | – | – | – |
| Trehalose | – | – | – | – |
| D-Sorbit | – | – | – | – |
| D-Mannit | – | – | – | – |
| Inosit | – | – | – | – |

TABLE 2-continued

| | | | | |
|---|---|---|---|---|
| Glycerin | − | − | − | − |
| Starch | − | − | − | − |

Note 1:
With regard to the physiological properties, +, ± and − mean the following.
+ the property or generation was observed
± difficult to judge the property or generation
− the property or generation was not observed Note 2:
Observation of generation of acid and evolution of gas from saccharides by bacteria in Hugh and Leifson media containing various saccharides as a carbon source.
+ generation of acid or evolution of gas was observed
± difficult to judge generation of acid or evolution of gas
− no generation of acid or evolution of gas was observed

*Pseudomonas putida* D4014 strain, which is a parent strain of *Pseudomonas putida* D4014-A357-3A strain, is a bacterium belonging to *Pseudomonas putida* [see JP-B-3-69918]. Because a mutant strain is generally considered to belong to the same species as does the parent strain, and in view of the mycological properties shown in the above-mentioned Table 1, *Pseudomonas putida* D4014-A357-3A strain was determined to belong to *Pseudomonas putida*.

*Pseudomonas putida* D4014 strain was originally deposited on Feb. 5, 1982 at the National Institute of Advanced Industrial Science and Technology, International Patent Organism Depositary (Chuo Dai-6, 1-1, Higashi 1-chome, Tsukuba-shi, Ibaraki 305-8566 Japan), accepted under the accession number: FERM P-6325, transferred to and accepted on Nov. 1, 1982 as the deposit based on the Budapest Treaty and has been preserved under accession number: FERM BP-205.

In addition, *Pseudomonas putida* D4014-A357-3A strain was originally deposited on Jun. 1, 2001 at the National Institute of Advanced Industrial Science and Technology, International Patent Organism Depositary (Chuo Dai-6, 1-1, Higashi 1-chome, Tsukuba-shi, Ibaraki 305-8566 Japan), accepted under accession number: FERM P-18361, transferred to and accepted on Jun. 10, 2002 as the deposit based on the Budapest Treaty and has been preserved under accession number: FERM BP-8070.

The production of 7α-hydroxy-pregn-4-en-3-one-20-carbaldehyde according to the present invention includes culturing a bacterium belonging to the genus *Pseudomonas*, which produces 7α-hydroxy-pregn-4-en-3-one-20-carbaldehyde from 3α,7α-dihydroxy-5β-cholanic acid and/or a salt thereof as a substrate in a medium containing 3α,7α-dihydroxy-5β-cholanic acid and/or a salt thereof.

The salt of 3α,7α-dihydroxy-5β-cholanic acid is exemplified by alkali metal salts (e.g., sodium salt, potassium salt etc.) of 3α,7α-dihydroxy-5β-cholanic acid, alkaline earth metal salts (e.g., calcium salt, magnesium salt etc.) thereof and the like. The concentration of 3α,7α-dihydroxy-5β-cholanic acid and/or a salt thereof in the medium is preferably in the range of 1–30 g/L, more preferably in the range of 5–20 g/L, from the aspects of isolation efficiency, inhibitory activity against bacteria and the like.

The medium may be any as long as it contains a nutrition source that the above-mentioned bacterium belonging to the genus *Pseudomonas* can utilize by assimilation. As the carbon source, 3α,7α-dihydroxy-5β-cholanic acid and/or a salt thereof may be used as a single carbon source, or 3α,7α-dihydroxy-5β-cholanic acid and/or a salt thereof may be used in combination with glucose, glycerin, peptone, meat extract, yeast extract and the like. As the nitrogen source, for example, inorganic nitrogen sources such as ammonium sulfate, ammonium chloride, ammonium phosphate, ammonium nitrate, sodium nitrate, potassium nitrate and the like; organic nitrogen sources such as peptone, meat extract, yeast extract and the like; and the like can be used. Besides these, inorganic salts such as dipotassium hydrogen phosphate, potassium dihydrogen phosphate, magnesium sulfate and the like are added.

While the culture conditions are free of any particular limitation, culture temperature is preferably in the range of 28–32° C., more preferably 29–31° C. The pH of the medium is preferably in the range of 7 to 9, more preferably 7.7 to 8.6. The culture time is preferably in the range of 12 hr-3 days. Culture is conducted under aerobic conditions by, for example, shake culture, agitation culture with aeration and the like.

By culture of bacterium in this manner, the starting material (3α,7α-dihydroxy-5β-cholanic acid and/or a salt thereof) is converted by the bacterium and 7α-hydroxy-pregn-4-en-3-one-20-carbaldehyde is accumulated in the culture solution. In this case, since the accumulated 7α-hydroxy-pregn-4-en-3-one-20-carbaldehyde has a markedly lower solubility in water as compared to the substrate (3α,7α-dihydroxy-5β-cholanic acid and/or a salt thereof), it precipitates in the culture solution. The 7α-hydroxy-pregn-4-en-3-one-20-carbaldehyde can be separated and harvested by, for example, standing still a culture solution containing the precipitated 7α-hydroxy-pregn-4-en-3-one-20-carbaldehyde, and decantation from a culture solution containing the floating bacterium, or adding methanol to a mixture containing the bacterium and 7α-hydroxy-pregn-4-en-3-one-20-carbaldehyde, which is obtained by centrifugation or an operation using a filtering aid, to dissolve 7α-hydroxy-pregn-4-en-3-one-20-carbaldehyde and evaporating methanol under reduced pressure from a methanol solution obtained by removing the bacterium and other insoluble materials. In this case, when water is added to evaporate methanol, 7α-hydroxy-pregn-4-en-3-one-20-carbaldehyde precipitates as needle crystals which are easy to separate and collect.

The production method of 7α,21-dihydroxy-20-methyl-pregn-4-en-3-one is explained next.

As the reducing agent, for example, borohydride compounds such as lithium borohydride, sodium borohydride, potassium borohydride, lithium cyanoborohydride, sodium cyanoborohydride, potassium cyanoborohydride, lithium tri-sec-butylborohydride, sodium tri-sec-butylborohydride, potassium tri-sec-butylborohydride, lithium triethylborohydride, sodium triethylborohydride, potassium triethylborohydride, lithium triacetoxyborohydride, sodium triacetoxyborohydride, potassium triacetoxyborohydride, tetrabutylammonium borohydride, tetrabutylammonium cyanoborohydride and the like; aluminum hydride compounds such as dimethyl aluminum hydride, diethyl aluminum hydride, dipropyl aluminum hydride, diisobutyl aluminum hydride, dimethoxy aluminum sodium hydride, trimethoxy aluminum sodium hydride, bis(2-methoxyethoxy)aluminum sodium hydride and the like; and the like can be mentioned. The amount of the reducing agent to be used is preferably an amount corresponding to not less than 1 molar equivalent, more preferably 1–5 molar equivalents, relative to 7α-hydroxy-pregn-4-en-3-one-20-carbaldehyde, when calculated in terms of hydrogen atom in the reducing agent.

The reaction can be carried out in the presence or absence of a solvent. The solvent is not particularly limited as long as it does not adversely influence the reaction and may be, for example, alcohols such as methanol, ethanol, n-propanol, isopropanol, n-butanol, 2-butanol, 2-methylpropanol and the like; ethers such as diethyl ether, diisopropyl ether, tetrahydrofuran, dimethoxyethane and the like; hydrocarbons such as pentane, hexane, cyclohexane, heptane, octane, petroleum ether, benzene, toluene and the like; and the like. These may be used alone or in combination of two or more kinds thereof. While the amount of the solvent to be used is not particularly limited, it is preferably 1 to 100-fold weight amount relative to 7α-hydroxy-pregn-4-en-3-one-20-carbaldehyde.

The reaction temperature is preferably in the range of −80° C. to 200° C., more preferably −20° C. to 180° C.

The reaction is carried out by adding 7α-hydroxy-pregn-4-en-3-one-20-carbaldehyde to a reducing agent, or adding a reducing agent to 7α-hydroxy-pregn-4-en-3-one-20-carbaldehyde and stirring the mixture at a predetermined temperature. Where necessary, 7α-hydroxy-pregn-4-en-3-one-20-carbaldehyde and the reducing agent may be used in the form of a solution in the above-mentioned solvent.

7α,21-Dihydroxy-20-methyl-pregn-4-en-3-one thus obtained can be isolated and purified by a method generally used for isolation and purification of an organic compound. For example, the reaction mixture is poured into a dilute acid such as dilute hydrochloric acid, dilute sulfuric acid and the like; dilute aqueous alkaline solution such as saturated aqueous sodium hydrogen carbonate solution, dilute aqueous sodium hydroxide solution and the like, brine or water, extracted with an organic solvent such as diethyl ether, ethyl acetate, methylene chloride and the like, and where necessary, the extract is washed-with saturated aqueous sodium hydrogen carbonate solution and the like to remove acidic substances, then washed with dilute hydrochloric acid, water,-brine and the like to remove basic substances and water-soluble substances, dried over anhydrous magnesium sulfate, anhydrous sodium sulfate-and the-like and concentrated to give a crude product, which is purified as necessary by distillation, chromatography, recrystallization and the like.

7α,21-Dihydroxy-20-methyl-pregn-4-en-3-one, for example, (20S)-7α,21-dihydroxy-20-methyl-pregn-4-en-3-one, can be converted to squalamine according to the method described in Org. Lett., Vol. 2, p. 2921 (2000).

EXAMPLES

The present invention is explained in more detail in the following by referring to Examples, which are not to be construed as limitative.

Reference Example 1

Method for Obtaining *Pseudomonas putida* D4014-A357-3A Strain

One loopful of *Pseudomonas putida* D4014 (FERM BP-205) strain grown overnight in a slant medium of Medium 1 (nutrient agar) was inoculated to 10 ml of Medium 2 (bouillon liquid medium) prepared in advance in a test tube, and shake-cultured at 30° C., 200 rps overnight. The obtained culture broth (1 ml) was inoculated to 10 ml of Medium 2 (as mentioned above) prepared in advance in a test tube, and shake-cultured for 6 hr. The obtained culture broth was aseptically passed through a 0.45 μm membrane filter to collect bacterial cells, which was washed with 0.1 M phosphate buffer (20 ml) and the bacterial cells adhered to the filter were suspended in the same buffer (25 ml). N-Methyl-N'-nitro-N-nitrosoguanidine was added to 4 ml of the obtained bacterial solution such that the final concentration was 50 μg/ml and the mixture was shaken at 30° C. for 10 min, whereby a mutation treatment was performed. The bacterial solution after the mutation treatment was immediately diluted 10-fold with the above-mentioned phosphate buffer, and this was diluted and spread on a plate medium of Medium 1, so that 500–1000 bacterial colonies would be formed, and the plate was subjected to standing culture overnight at 30° C. The emerged colonies were randomly picked up (50 colonies/plate) on the plate medium of Medium 1, and each was inoculated to a slant medium of Medium 1 (as mentioned above) the next day. The bacterial strains grown and obtained in this way were inoculated by 2 loopfuls into a test tube containing 10 ml of Medium 3 (composition: 3α,7α-dihydroxy-5β-cholanic acid 10 g, sodium hydroxide 1.1 g, ammonium nitrate 2 g, monopotassium dihydrogen phosphate 1 g, dipotassium hydrogen phosphate 6 g, magnesium sulfate 0.5 g, peptone 0.5 g, yeast extract 0.5 g, glucose 0.5 g, tap water 1 L, pH 7.8) sterilized in advance and subjected to shake culture at 30° C., 200 rps for 24 hr. The product in each obtained culture broth was detected by thin layer chromatography and one bacterial strain selectively accumulating the object 7α-hydroxy-pregn-4-en-3-one-20-carbaldehyde was found, which was named *Pseudomonas putida* D4014-A357-3A.

Example 1

Obtainment of (20S)-7α-hydroxy-pregn-4-en-3-one-20-carbaldehyde

*Pseudomonas putida* D4014-A357-3A strain was inoculated to a slant medium of Medium 1 (as mentioned above) and cultured at 30° C. for one day. Then, 2 loopfuls of the bacterial cells grown were inoculated to a liquid medium (10 ml) of Medium 3 (as mentioned above) containing 3α,7α-dihydroxy-5β-cholanic acid and subjected to shake culture at 30° C. overnight. The obtained culture broth was inoculated to 100 ml of Medium 3 (as mentioned above) having the same composition in a 500 ml Sakaguchi flask and cultured at 30° C., 200 rps for 48 hr. The total amount of 3α,7α-dihydroxy-5β-cholanic acid subjected to the culture was 1.1 g (2.8 mmol). The obtained culture broth was centrifuged at 5000 rpm for 30 min, and water (100 ml) was added to a mixture of the obtained bacterial cells and the product to allow dispersing. The mixture was again subjected to centrifugation to wash the mixture. Methanol (200 ml) was added to the mixture to dissolve the product, and the mixture was filtered to give a clear methanol solution. Water (30 ml) was added to the methanol solution and methanol was partly evaporated in a rotary evaporator. Then, the resulting concentrate was cooled, and the precipitated solid was collected by filtration and dried to give (20S)-7α-hydroxy-pregn-4-en-3-one-20-carbaldehyde (310 mg, 0.90 mmol, yield 32%) having the following property.

The obtained (20S)-7α-hydroxy-pregn-4-en-3-one-20-carbaldehyde was partly taken and methanol was added thereto to give a 1% solution. This solution was applied to high performance liquid chromatography (pump part; Model 510 manufactured by Waters, Inc.) equipped with ODS-80™ (trade name, manufactured by TOSOH CORPORATION, 4.6 mm×150 mm) column (column temperature 40° C., column oven; Shimadzu CTO-6A, manufactured by SHIMADZU CORPORATION). As a mobile phase, water/methanol=27/73 (phosphoric acid 50 μl/L added) was flown at 1 ml/min, and detection was done using a refractive index system (detector; Shodex RI-71 manufactured by SHOWA DENKO K.K.). The purity of the above-mentioned (20S)-7α-hydroxy-pregn-4-en-3-one-20-carbaldehyde was determined from the area ratio of each peak in the obtained chromatogram (data processing; Shimadzu C-R7A plus, manufactured by SHIMADZU CORPORATION) and found to be 96%.

$^1$H-NMR spectrum (270 MHz, CDCl$_3$, TMS standard, ppm) δ: 9.568 (1H, d, J=3.95 Hz), 5.427 (1H, d, J=1.98 Hz), 3.97–3.98 (1H, bs), 2.635 (1H, ddd, J=2.96, 2.96, 14.84 Hz), 2.30–2.55 (4H, m), 1.10–2.10 (14H, m), 1.205 (3H, s), 1.139 (3H, d, J=5.94 Hz), 0.769 (3H, s)

Example 2

Synthesis of (20S)-7α,21-dihydroxy-20-methyl-pregn-4-en-3-one

Ethanol (20 ml) was added to (20S)-7α-hydroxy-pregn-4-en-3-one-20-carbaldehyde (2.00 g, 5.81 mmol) obtained in the same manner as in Example 1 and the mixture was ice-cooled with stirring. Sodium borohydride (0.11 g, 2.91 mmol) was added to the obtained solution and the mixture was stirred under ice-cooling for 1 hr. 3% Hydrochloric acid was added to the obtained reaction mixture for neutralization, and ethanol was evaporated under reduced pressure. Ethyl acetate (100 ml) and water (20 ml) were added to wash the residue, and the aqueous layer was separated. The organic layer was dried over anhydrous sodium sulfate, filtered and concentrated under reduced pressure to give (20S)-7α,21-dihydroxy-20-methyl-pregn-4-en-3-one (1.77 g, yield 88%) having the following property.

$^1$H-NMR spectrum (270 MHz, CDCl$_3$, TMS standard, ppm) δ: 5.796 (1H, s), 3.965 (1H, brd, J=1.98 Hz), 3.632 (1H, dd, J=2.96, 10.88 Hz), 3.371 (1H, dd, J=6.92, 10.88 Hz), 2.612 (1H, ddd, J=2.97, 2.97, 14.84 Hz), 2.415 (1H, dd, J=2.97, 14.84 Hz), 2.3–2.5 (m, 2H), 1.0–2.1 (m,15H), 1.194 (3H, s), 1.052 (3H, d, J=6.92 Hz), 0.740 (3H, s).

INDUSTRIAL APPLICABILITY

According to the present invention, 7α-hydroxy-pregn-4-en-3-one-20-carbaldehyde and 7α,21-dihydroxy-20-methyl-pregn-4-en-3-one useful as synthetic intermediates for pharmaceuticals such as squalamine and the like can be produced efficiently at high purity.

The invention claimed is:

1. 7α-hydroxy-pregn-4-en-3-one-20-carbaldehyde.

2. A production method of 7α-hydroxy-pregn-4-en-3-one-20-carbaldehyde, which comprises culturing a bacterium belonging to the genus *Pseudomonas*, which produces 7α-hydroxy-pregn-4-en-3-one-20-carbaldehyde from 3α,7α-dihydroxy-5β-cholanic acid and/or a salt thereof as a substrate in a medium containing 3α,7α-dihydroxy-5β-cholanic acid and/or a salt thereof.

3. The production method of claim 2, wherein the bacterium belonging to the genus *Pseudomonas* is *Pseudomonas putida* D4014-A357-3A strain (FERM BP-8070).

4. A production method of 7α,21-dihydroxy-20-methyl-pregn-4-en-3-one, which comprises reacting a reducing agent with 7α-hydroxy-pregn-4-en-3-one-20-carbaldehyde.

5. The production method of claim 4, wherein the reducing agent is a borohydride compound or an aluminum hydride compound.

6. The production method of claim 4, wherein the reducing agent is used in an amount of not less than 1 molar equivalent relative to 7α-hydroxy-pregn-4-en-3-one-20-carbaldehyde, as calculated in terms of hydrogen atom in the reducing agent.

7. The production method of claim 4, wherein the reaction is carried out at a temperature of −80° C. to 200° C.

* * * * *